(12) United States Patent
Thomke et al.

(10) Patent No.: US 8,206,388 B2
(45) Date of Patent: Jun. 26, 2012

(54) INSERT FOR A CLAMPING ELEMENT, CLAMPING ELEMENT COMPRISING SAID INSERT AND UNIVERSAL JOINT PRODUCED THEREFROM

(75) Inventors: Roland Thomke, Bellach (CH); Damian Fankhauser, Bern (CH)

(73) Assignee: Stryker Trauma S.A. (CH)

( * ) Notice: Subject to any disclaimer, the term of this patent is extended or adjusted under 35 U.S.C. 154(b) by 714 days.

(21) Appl. No.: 11/632,191

(22) PCT Filed: Nov. 30, 2005

(86) PCT No.: PCT/CH2005/000714
§ 371 (c)(1),
(2), (4) Date: Jan. 17, 2007

(87) PCT Pub. No.: WO2006/058449
PCT Pub. Date: Jun. 8, 2006

(65) Prior Publication Data
US 2008/0065068 A1    Mar. 13, 2008

(30) Foreign Application Priority Data
Nov. 30, 2004  (EP) ..................................... 04405743

(51) Int. Cl.
*A61F 5/04* (2006.01)
(52) U.S. Cl. .......................................... 606/59; 606/324
(58) Field of Classification Search ............... 24/135 A, 24/135 R, 168, 484, 485, 487, 507; 403/289, 403/290, 310–314, 350–352, 385, 390, 399; 439/435, 574, 761, 822; 606/151, 277, 278, 606/324, 54, 56, 59; 600/227, 228–230
See application file for complete search history.

(56) References Cited

U.S. PATENT DOCUMENTS

| 2,803,349 | A |   | 8/1957  | Talbot |
|-----------|---|---|---------|--------|
| 4,310,209 | A | * | 1/1982  | Fleming et al. ................. 439/99 |
| 4,365,624 | A |   | 12/1982 | Jaquet et al. |
| 4,696,293 | A |   | 9/1987  | Ciullo |
| 4,821,382 | A |   | 4/1989  | Puschkarski et al. |
| 5,312,405 | A | * | 5/1994  | Korotko et al. ............... 606/278 |
| 5,769,556 | A |   | 6/1998  | Colley |

(Continued)

FOREIGN PATENT DOCUMENTS
EP     0700664     3/1996
(Continued)

OTHER PUBLICATIONS
International Search Report, PCT/CH2005/000714.
(Continued)

*Primary Examiner* — Eduardo C Robert
*Assistant Examiner* — Lynnsy Schneider
(74) *Attorney, Agent, or Firm* — Lerner, David, Littenberg, Krumholz & Mentlik, LLP

(57) ABSTRACT

An insert for a clamping element having two jaws for clamping a rod-shaped element comprises at least one jacket element. The jacket element can be inserted into one jaw each of the clamping element, thereby allowing the varying, especially reducing, the free space available for a rod. The insert also comprises at least one retaining section which fastens at least one part of the insert in or on at least one of the jaws of the clamping element. A clamping element can be provided with two jacket elements, interlinked via an undulated web, or two or three juxtaposed longitudinal grooves for receiving rods having different diameters.

16 Claims, 13 Drawing Sheets

U.S. PATENT DOCUMENTS

| | | |
|---|---|---|
| 6,277,069 B1 | 8/2001 | Gray et al. |
| 6,312,377 B1 * | 11/2001 | Segermark et al. ............ 600/232 |
| 6,616,664 B2 | 9/2003 | Walulik et al. |
| 6,652,523 B1 | 11/2003 | Evrard et al. |
| 7,182,301 B1 * | 2/2007 | Oddsen et al. .............. 248/122.1 |
| 7,270,665 B2 * | 9/2007 | Morrison et al. .............. 606/300 |
| 7,527,626 B2 * | 5/2009 | Lutz et al. ........................ 606/54 |
| 2002/0165543 A1 * | 11/2002 | Winquist et al. ................. 606/54 |
| 2003/0028192 A1 * | 2/2003 | Schar et al. ...................... 606/61 |

FOREIGN PATENT DOCUMENTS

| | | | |
|---|---|---|---|
| EP | 1184000 | | 3/2002 |
| GB | 1079786 | | 8/1967 |
| GB | 2029490 | * | 9/1978 |
| GB | 2029490 | | 3/1980 |
| GB | 2033758 | | 5/1980 |
| WO | 9605777 | | 2/1996 |
| WO | 2005085658 | | 9/2005 |

OTHER PUBLICATIONS

ROMER JOCKEY Classic, Bicycle Seat for Children: Instructions for Insatllation and Use.

Office Action from Japanese Application No. 2007-541637 dated Aug. 18, 2011.

* cited by examiner

INSERT FOR A CLAMPING ELEMENT, CLAMPING ELEMENT COMPRISING SAID INSERT AND UNIVERSAL JOINT PRODUCED THEREFROM

TECHNICAL FIELD OF THE INVENTION

The invention concerns an insert for a clamping element for clamping a rod-shaped element of a universal joint, particularly for a clamping element of a universal joint for stabilizing bone fractures. Furthermore, the invention concerns a universal joint with two clamping elements and with one locking element.

Prior Art

EP 1 184 000 describes a one-piece element that has two opposing jaws and one free space that opens to the side for receiving a rod-shaped element and a hinge placed opposite the free space, that connects the jaws to one another and by means of which these are movable, whereby each jaw has one bore, and which are aligned with each other.

This clamping element has the advantage that with two identical clamping elements placed one next to the other, a universal joint may be produced whereby through the said bores, a connecting screw may be inserted, which is screwed into an interior-threaded nut, in order to close the clamping jaws.

A disadvantage of the known device is that the rod-shaped elements may be inserted into the receiving free spaces only from their ends in a lengthwise direction.

Another clamping element is known from U.S. Pat. No. 6,277,069, which is open on the side. This permits the lateral insertion of a first rod-shaped element. A second rod-shaped element may be introduced into a closed casing connected to a tension lever.

A universal joint is known from both U.S. Pat. No. 6,616,664 and EP 0 700 664, that is composed of four individual clamping jaw elements and one central screw. With this universal joint it is possible to introduce one or two rod-shaped elements laterally into the corresponding free spaces. In EP 0 700 664 a spring is arranged between the two center clamping jaw elements, against the spring tension of which it is possible to clip in the rod-shaped elements and thus to hold the universal joint to the rod-shaped elements before locking it. In U.S. Pat. No. 6,616,664 narrow, laterally-placed lever arms are provided in order to hold laterally-inserted rod-shaped elements before locking of the universal joint.

A disadvantage of these devices lies in the fact that the clamping elements of such a universal joint must be designed for the diameter of the rod or pin to be inserted. Thus the surgeon must have available a series of different clamping elements, in order to take into account the conditions of a particular operation.

Starting with this prior art, it is the object of this invention to present an insert for a clamping element that allows the lateral insertion of rod-shaped elements of varying thicknesses.

It is further the object of this invention to present a clamping element for the simple insertion of such inserts that allows the lateral insertion of rod-shaped elements of varying thicknesses, in particular at least the insertion of two different rods in two clamping elements of a universal joint.

A further goal of the invention is to create a cost-effective single-use clamping element, in particular made of injection-molded plastic, which is subsequently adaptable for various different rod-shaped elements.

Starting from the known prior art, the invention also has the object of presenting an improved universal joint.

Abstract of the Invention

Pursuant to the invention, this problem is solved for an insert of the type described in the introduction with the characterizing features of claim 1. A kit made up of such inserts is described in claim 10. A corresponding clamping element is described by means of the features in claim 11. A universal joint pursuant to the invention is described in claim 13.

Through the fact that the clamping elements may subsequently be equipped with inserts, the size of the jaws of the two clamping elements may be adjusted to each other, in order to be designed in a simple manner for varying rod-shaped elements of an articulated element.

On the other hand, clamping elements that already have inserts, in one or more of the jaws, may be provided and supplied, which, upon actual use may easily be removed. If the inserts are formed from an isolating material, it is possible to avoid the formation of a conducting circuit through an external fixator and thus contribute to the MRI safety of such a fixator.

An essential advantage of the clamping elements pursuant to the invention lies in the possibility, by using a clever combination of materials, of attaining a good grip on the rod-shaped elements. In particular, the insert may consist of a softer, more plastic material than the clamping element or the rod, so that an increased and improved static friction between insert and rod and insert and jaw of the clamping element occurs than would be possible in direct contact.

Additional advantageous embodiments are set forth in the subordinate claims.

BRIEF DESCRIPTION OF FIGURES

The invention will now be described in greater detail, making reference to the drawings and using embodiments as examples.

The figures show.

DETAILED DESCRIPTION OF THE PREFERRED EMBODIMENTS

Figure 1:
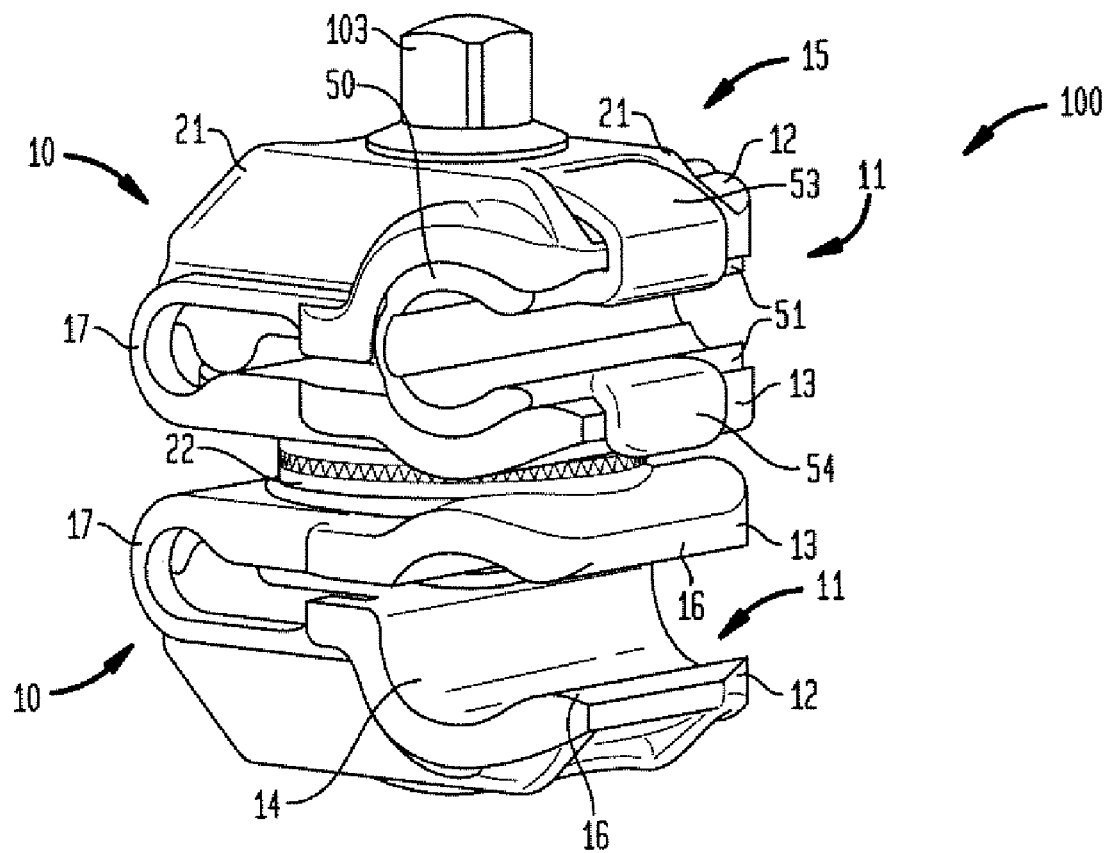
FIG. 1 a perspective view of an articulated element with two clamping elements with one insert pursuant to the invention, FIG. 2 a perspective view of the insert according to the first embodiment for a clamping element according to FIG. 1, FIG. 3 a side view of the insert according to FIG. 2, FIG. 4 a perspective representation of an articulated element according to FIG. 1 in a locked position with two clamped rod-shaped elements and one insert according to FIG. 2, FIG. 5 a perspective view of an insert according to a second embodiment for a clamping element according to FIG. 1, FIG. 6 a side view of the insert according to FIG. 5, FIG. 7 a side view of an articulated element according to FIG. 1 with an insert according to FIG. 5, FIG. 8 a perspective view of an insert according to a third embodiment for a clamping element according to FIG. 1, FIG. 9 a side view of an insert according to FIG. 8, FIG. 10 a perspective view of an insert according to a fourth embodiment for a clamping element, FIG. 11 a side view of the insert according to FIG. 10, FIG. 12 another perspective view of the insert according to FIG. 10, diagonally from below, FIG. 13 a perspective view of another articulated element with an insert according to FIG. 10 and a clamped rod, FIG. 14 a side view of the articulated element according to FIG. 13, FIG. 15 a perspective view of an insert according to a fifth embodiment for a clamping element, FIG. 16 a side view of the insert according to FIG. 15, FIG. 17 a top view of the insert according to FIG. 15, FIG. 18 a detail from an external fixator with several articulated elements and various rods of differing configurations held by these FIG. 19 a perspective view of an insert according to a sixth embodiment for a clamping element according to FIG. 1, FIG. 20 a side view of the insert according to FIG. 19, FIG. 21 a perspective view of an insert according to a seventh embodiment for a clamping element according to FIG. 1, FIG. 22 a side view of the insert according to FIG. 21, and FIG. 23 a sectional front view of the insert according to FIG. 21.

FIG. 1 shows a perspective view of a first embodiment of an articulated element 100 with two clamping elements 10 with an insert 50 pursuant to the invention. Each clamping element 10 has two opposing clamping jaws 12 and 13 having a free space 11 to receive a rod-shaped element. The clamping jaws 12 and 13 on their free ends 15 each have a transverse groove 14, which together span the free space 11. On the free ends 15, the outer edges 16 of the sides of the clamping jaws 12 and 13 that face each other are angled in order to simplify the pushing in of a rod-shaped element from the side. Opposite the free space 11 and the free ends 15, a hinge 17 is provided, which connects the clamping jaws 12 and 13 into a single piece. A screw 103 that passes through the clamping elements 10, closes the articulated element 100 and clamps rods to be inserted into it. This is a locking element, which may also be realized by means of levers and other elements.

The clamping elements 10 have in their center area a full material transverse cut, which form two lateral transverse ribs 21, which are particularly pronounced in the upper area of clamping jaw 12. The area between the transverse ribs 21 is hollowed out form the front edge 16 to a round screw mounting visible in the top view. The screw mounting may, for example, have a conical shoulder surface or a stepped shoulder and is graduated to receive the screw 103 in a through bore in the upper clamping jaw 12. The ribs may also run entirely along the outer side of the clamping element.

In the lower clamping jaw 13, said transverse ribs 21 lead into a ring flange 22, which may, for example, have a flat ring-shaped base, which may be connected to a recess produced by injection molding, to save materials and weight, and in the center of which a bore is provided. This through bore is placed so as to be aligned with the aforementioned though bore in the upper clamping jaw 12. It runs through the clamping element 10 perpendicular to the axis of the free space 11 and parallel to the back side of the hinge 17. But it could also run diagonally.

In the representation in FIG. 1, the articulated element 100 is formed from two clamping elements 10. The lower clamping element 10 is intended for a rod with a diameter of, for example, 12 millimeters. Then the opening on the free end has a diameter of, for example, 8 millimeters, at rest. If the upper clamping element 10 is to be intended for rod with a diameter of 4 to 6 millimeters, then the opening on the free end 15 should have a diameter of, for example, 2 millimeters at rest.

In the free space 11, an insert 50 is inserted that consists of two curved surfaces 51 in the form of hollow quarter-circle cylinders, which are connected to each other by a web 52. These sections may also be termed jacket elements 51. The web 52 in its radial direction is specifically thinner than the curved surfaces 51. The curved surfaces 51 with their outer surfaces 56 in the shape of the outer cylinder jackets touch the inner surfaces of the grooves 14. The insert 50 used in FIG. 1 includes two retaining tongues 53 and 54 that extend away from the interior space 58 of the insert 50 and that particularly with the insert with a clamping element 10, extend between the said ribs 21. Thus the insert 50 is held securely against axial displacement in the direction of the rod to be inserted. By means of the two tongues 53 and 54, a twisting of the insert is also prevented. The rounded outer surfaces 55 of the tongues 53, 54 in the transition to the curved surfaces 51 of the insert 50 form the insert edges 16 for a rod. The retaining tongues or clips 53 may in general be termed retaining sections.

Figure 2:
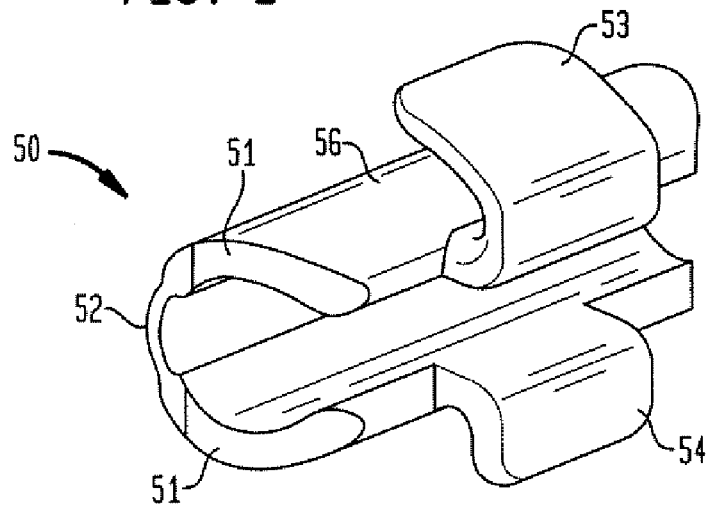
Figure 3:
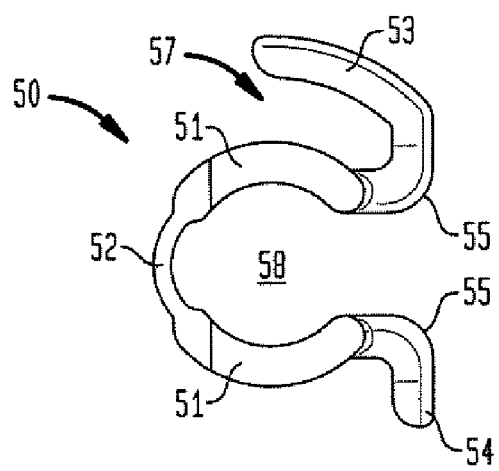

FIG. 2 shows a perspective view of the insert 50 according to the first embodiment for a clamping element 10 according to FIG. 1. FIG. 3 shows a side view of said insert 50 according to FIG. 2. The insert 50 is provided with an upper clip 53 oriented in the direction of the connecting web 52, whereby between the clip 53 and the outer surface 56, there is a clamping space 57, in which a portion of the upper clamping jaw 13 is inserted. The clip 53 may be so formed that at rest, i.e. placed in the direction of the outer surface, the insert 50, after its insertion in the clamping element 10, is held by the clip 53 under initial tension. The length of the upper clip 53 here is almost as long as the width of the quarter cylinder 51. The lower clip 54, on the other hand, is considerably shorter and is oriented perpendicular to the axis of the free space 11. The material thickness of the clips 53, 54 corresponds to that of the quarter cylinder 51 (here elements 51 according to FIGS. 2 and 3). The width of the clips 53 and 54 is advantageously between one-third and two-thirds of the width of the quarter cylinder 51. The width of the quarter cylinder 51 is preferably of the longitudinal size of the groove 11 of the jaws 12 or 13.

For other embodiments, not shown here, other clip forms are also possible. In particular, the upper clip 53 and/or the lower clip 54 may be made thinner and, in particular, complementary to a slot provided in the upper or lower clamping jaw 12 or 13. Such a slot would then run parallel to the main axis of a rod 101, 102 to be inserted. In this way, the insert may be pressed into clamping element 10 without projecting elements and thus held under continuous tension. The insert 50 may, for example, be a one-piece plastic element. It may also include a co-extruded plastic element with two different types of material, or a metallic element (as or in the hinge).

The connecting web 52 here has the same radius of curvature as the surfaces 51. It is only thinner and when subjected to stress, buckles forward into the free space 11 or backwards out of the free space 11.

Figure 4:
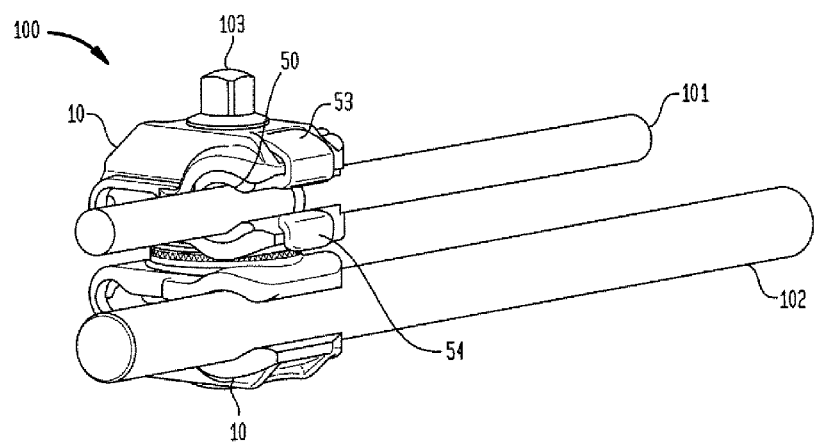

FIG. 4 shows a perspective representation of an articulated element 100 according to FIG. 1 in a locked position with two clamped rod-shaped elements 101 and 102 and an insert 50 according to FIG. 2.

Figure 5:
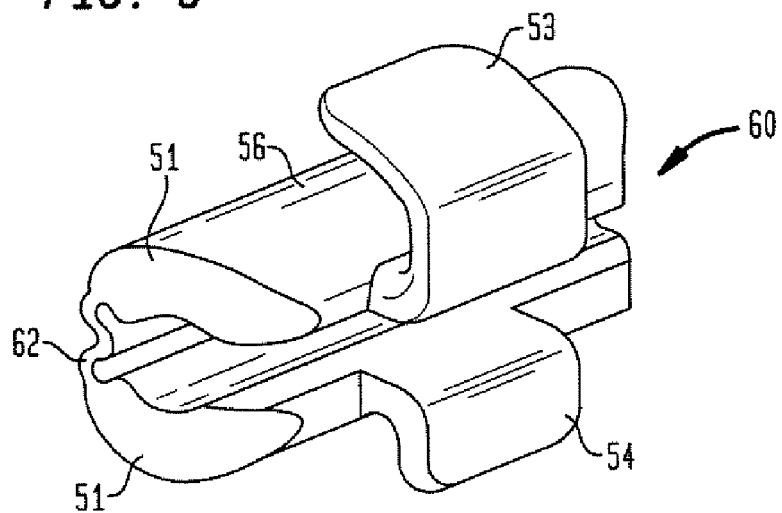
Figure 6:
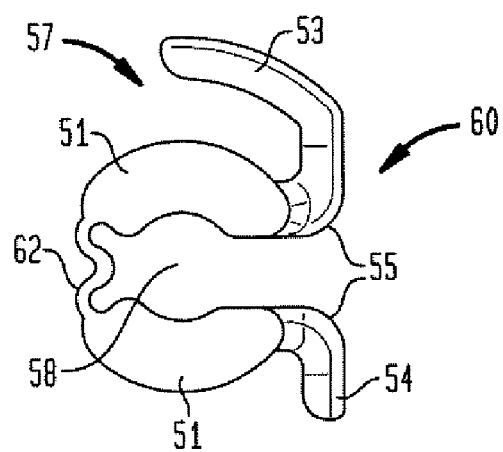

FIG. 5 now shows a perspective view, diagonally from above, of an insert 60 according to a second embodiment. FIG. 6 shows a side view of an insert 60 according to FIG. 5. The same features are provided in each case with the same reference numbers. The two main differences between the two inserts 50 and 60 according to FIG. 2 and FIG. 5 are that the insert 50 according to FIG. 2 is intended to receive a rod-shaped element of a larger diameter and the curved surfaces 51 of the insert 60 according to FIG. 5 have a greater material thickness. After insertion of the insert 60, however, the center axis of the free space 11 is still at the height of the slot. This is not true, for example, for an insert 80, see FIG. 14.

Furthermore, the insert 60 according to FIG. 5 has an undulated web 62. This web begins to be elongated at the thicker quarter cylinder 51, i.e. in a tangential direction, in order to form a cam bent inward toward the free space 58.

Thus a longer spring range is created for the web 62. The two clips 53 and 54 are shaped as in the first embodiment. The web 82 could also be shorter than the longitudinal length of the insert 50 or be interrupted.

In an embodiment not represented in the drawings, an insert according to FIG. 2 may consist of two separate parts, i.e. there is no web 52. Then two inserts may be used, of which, for example, one consists of surface 51 and clip 53 and another of surface 51 and clip 54. But two identical inserts are also possible. What is essential then is that these two inserts be clipped in above and below independently of each other.

The insert according to the embodiment of FIG. 5 is designed using a smaller rod-shaped element. Instead of this one insert 60, it is also possible, (according to an embodiment not represented in the drawings), to use two or more thin concentric shell inserts. Here it should be understood that in order to achieve the effect of a small opening 58 in an insert 50 according to FIG. 2, which is already inserted in FIG. 1, an additional shell insert is inserted, which is an insert that is placed concentric to the first insert 50. The inner shell insert then has a surface 51 that leans with its upper side 56 onto the inner side of the insert 50 and it will preferably have a clip that on the outside lies on the first clip 53. There may then also be a third shell insert, in order to reduce the opening 58 by one additional step. Thus a kit is formed, the different inserts of which form a sequence of jacket elements 51 which may be inserted concentrically into one another.

The embodiments described here are all designed concentrically with respect to the rod to be inserted. It should be noted already here—in anticipation of the embodiment according to FIG. 10—that a corresponding eccentric embodiment of the insert 50 or 60 is possible. This means that the quarter-circle cylinders 51 are so termed only for their outer surface 56, since these continue to touch a surface designed for a rod-shaped element. On the inner side, however, another asymmetric form may then be provided, which in cross section may, for example, be a triangular groove. This then allows the insertion of rods of various sizes, that are all positioned the same way with respect to one plane.

Figure 7:
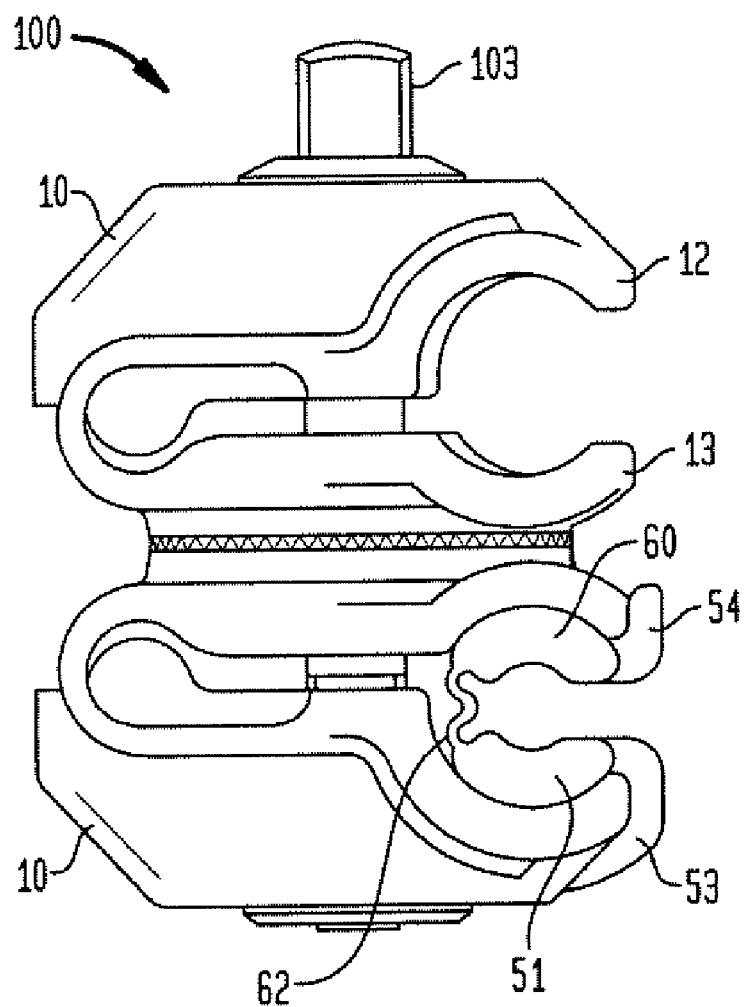

FIG. 7 shows a side view of an articulated element 100, as represented in FIG. 4, with an insert 60 according to FIG. 5 in the lower clamping element 10.

Figure 8:
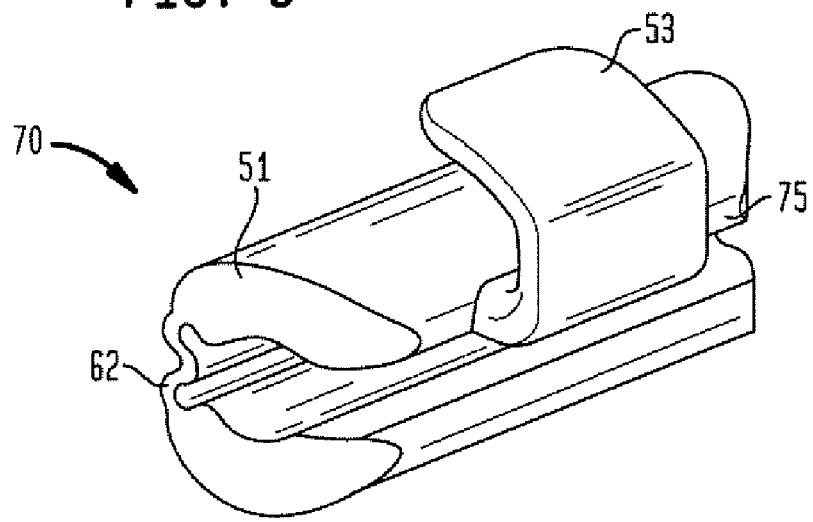
Figure 9:
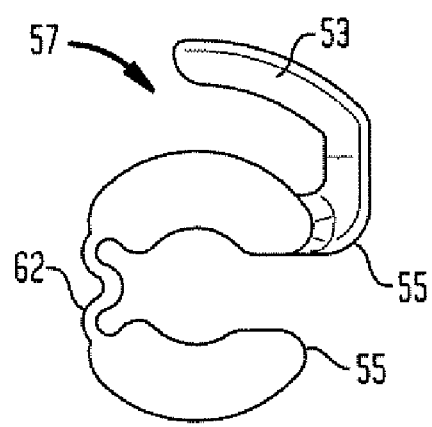

FIG. 8 shows a perspective view, diagonally from above, of an insert 70 according to a third embodiment. FIG. 9 shows a side view of the insert 60 according to FIG. 5. The sole difference between the two inserts 60 and 70 according to FIG. 5 and FIG. 8 is that the insert 70 according to FIG. 8 has only one clip 53. The clip 53 is provided for engagement in the area between the ribs 21 of the outer clamping jaw 12. Thus there is no clip for the inner clamping jaw 13; but the outer impression surface 55 extends over the entire length of the insert 70, while on the opposing side the impression surface 55 for a rod projects onto clip 53 and, as in the previously described embodiments, there is a back edge 75 to the right and left.

Figure 10:
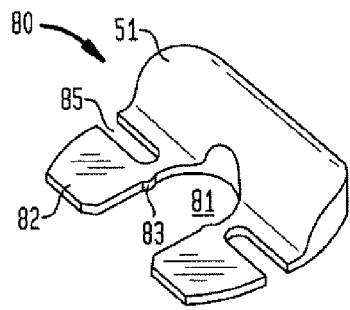
Figure 11:
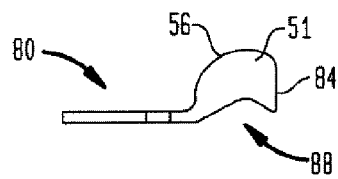
Figure 12:
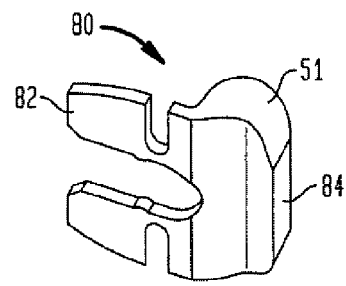

FIG. 10 shows a perspective view of an insert 80 according to a fourth embodiment, FIG. 11 a side view of the insert 80 according to FIG. 10, and FIG. 12 another perspective view of the insert 80 according to FIG. 10, diagonally from underneath. This insert 80 may be most easily explained with a look at FIG. 13, in which a perspective view of another articulated element 110 with two other clamping elements 20 and with an insert according to FIG. 10 and a rod 101, here a so-called "pin" clamped securely, is represented. The clamping element 20 essentially corresponds to a clamping element pursuant to EP 0 700 664.

The insert 80 has a quarter cylinder 51 that is still recognizable by its outer surface 56, but that has an underside that in section has a very reduced radius of curvature, and thus forms an upper boundary for a small free space 88. The insert 80 has an oval recess 81, going backwards in the top view, which thus forms a recess for the screw 103. As guide grooves, two projections 83 are provided in the recess 81. The thickened quarter cylinder 51, which with its outer surface 56 engages an outer jaw 12, passes over into a flat even web surface 82, which comes to rest between the outer jaw 12 and the inner jaw 13 of a clamping element 20. In this way the insert 80 is secured in its position in the articulated element 110.

Through the existence of the backward recess 81, two lateral webs 82 are created and the insert 80 may then be inserted sideways, as later a rod, into the articulated element 110, whereby before securing of the elements, the projections 83 hold the insert 80 in the articulated element 10. The front side 84 of the insert 80 then connects to the front side of the clamping element 20. The webs 82 each have side slots 85, which run in a radial direction to the main axis which runs transverse to it, and which corresponds to the orientation of the screw 103. In this way, it is also possible to insert a metallic insert 80, since if the screw 103 snaps onto the projections, the side webs 82 bend into the slots 85.

Figure 13:
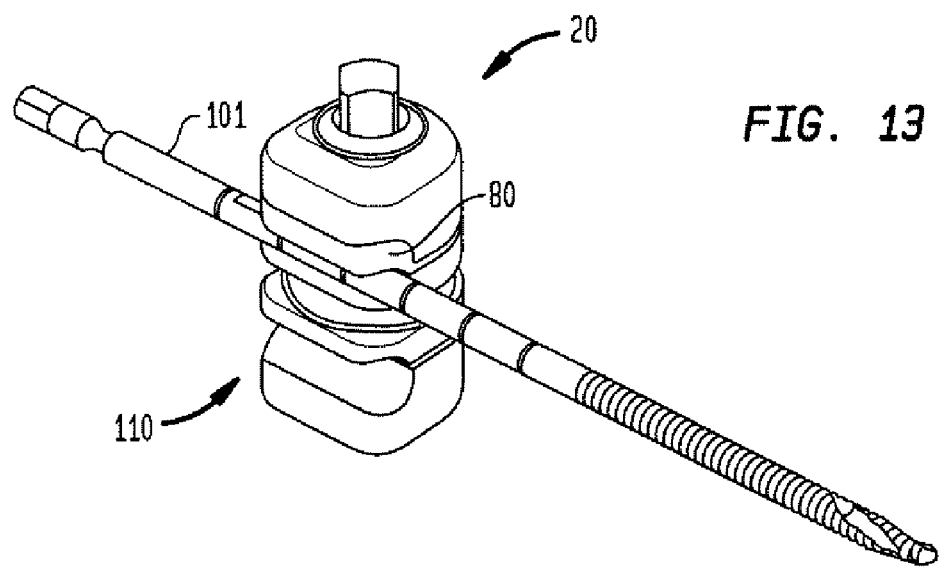
Figure 14:
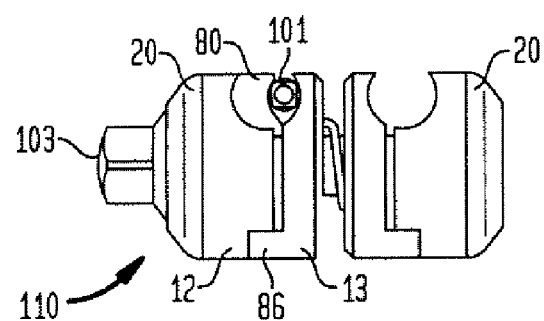

In FIG. 13 and FIG. 14, which represents a side view of the articulated element 120 according to FIG. 13, the application of insert 80 with a very thin rod or pin 101, having a diameter of 4 to 6 millimeters, is shown. It may be seen that in the fourth embodiment of insert 80, the pin 101 lies on one side on the inner jaw 13, while on the other side, it touches the insert 80. The insert 80 is shorter than the depth of the clamping element 20, since for anti-twist protection, the two jaws 12 and 13 are provided with recess or complementary projection 86.

Figure 15:
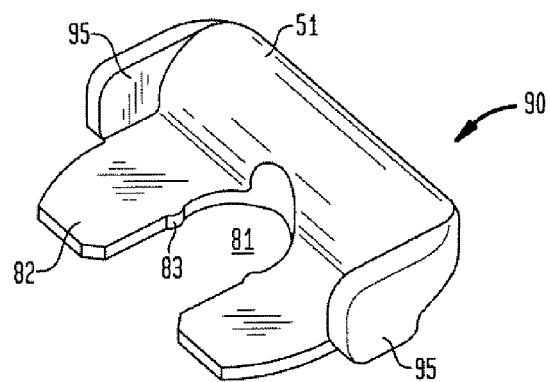
Figure 16:
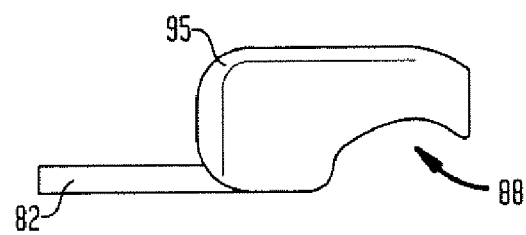
Figure 17:
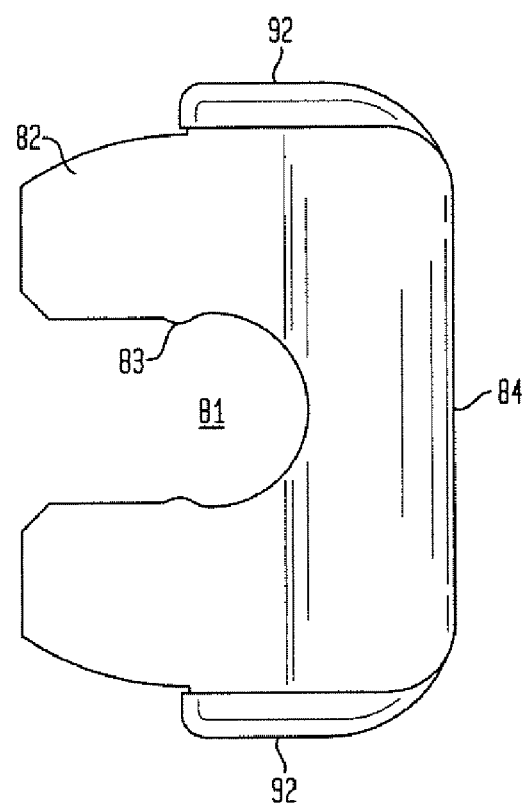

FIG. 15 shows a perspective view of an insert 90 according to a fifth embodiment for a clamping element 20, FIG. 16 a side view of the insert 90 according to FIG. 15, and FIG. 17 a top view of the insert 90 according to FIG. 15. The insert 90 according to FIG. 15, in contrast to the insert 80 according to FIG. 10, has side ribs 92, which may project next to the jaws 12 or 13 of the clamping element 20. They may also be fitted into corresponding recesses in the jaws 12 or 13. Thus, in addition to the anchoring deep inside the opening 81 around the screw 103, the insert 90 is also protected against lateral displacement. The additional features of this insert 90 correspond to those of the insert 80 according to FIG. 10.

Figure 18:
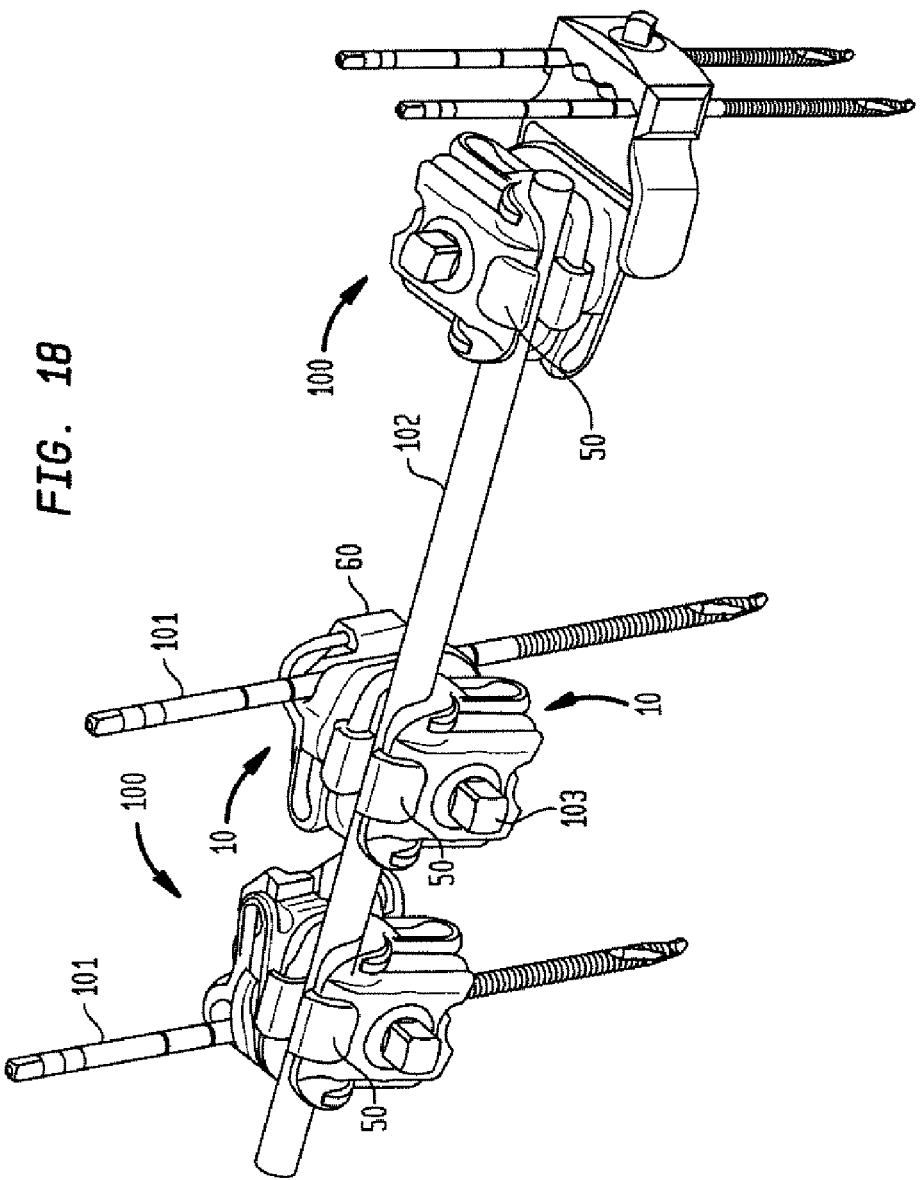

Finally, FIG. 18 shows a detail from an external fixator with several articulated elements 100 and various rods 101, 102 held by these, with various inserts 50 and 60 in different configurations. The articulated elements 100 are each constructed out of two clamping elements 10, with which a clamping of a thick rod, of 10 to 12 millimeters, is possible. The rod 102 of medium thickness used here has a diameter of between 6 and 8 millimeters and requires an insert 50 for the reduction and adaptation of the diameter of the rod to be clamped by, for example, 2 millimeters. In the other clamping element 10, an insert 60 is used for the reduction and adaptation of the diameter of the rod 101 to be clamped to, for example 4 millimeters, since the thinner rod 101 used here has a diameter of between 6 and 8 millimeters. It is thus clear that in using the clamping element 10 with no insert, with an insert 50 or with an insert 60, three possible rod thicknesses may be used.

In the embodiment according to FIG. 14, as a guide for the thin rod 101, in addition to the insert 80 on the opposite side on the bottom of the groove 14 of the lower clamping jaw 13, the two serrated elevations (not visible in the drawings) on both sides of groove 14 symmetrical to the center line, may be used. These support a thin rod that has been inserted each from the respective side.

The materials of the clamping elements 10, 20 and the inserts 50, 60, 70, 80, 90 may respectively be chosen from among plastic, fiber-reinforced plastic, metal and particularly titanium or a steel. It is also possible, as noted above, to use mixtures, in particular co-extruded elements. Interestingly, inserts 50, 60, 70, 80, 90 are of a softer plastic, which effectively prevents a longitudinal slippage or twisting of the rods 101, 102 in the insert. This also makes the use of thinner inserts practical, which are inserted not for reduction of thickness, but primarily or exclusively to improve the bond. Then the aforementioned quarter cylinders 51 are very thin and no thicker than the aforementioned web 52, 62.

The clips 53, 54 are not only guide- and fixing elements, but also operating elements. The clips 53 and 54 should be able to be gripped by the user in order to engage the inserts 50, 60 etc. and to take them out or insert them into a clamping element 10.

Figure 19:
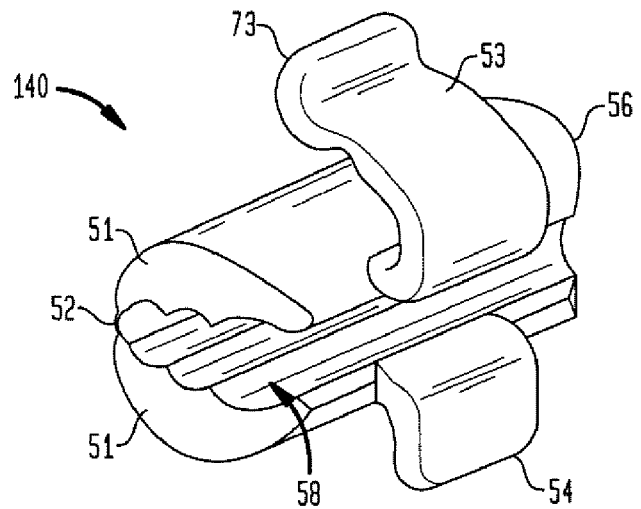
Figure 20:
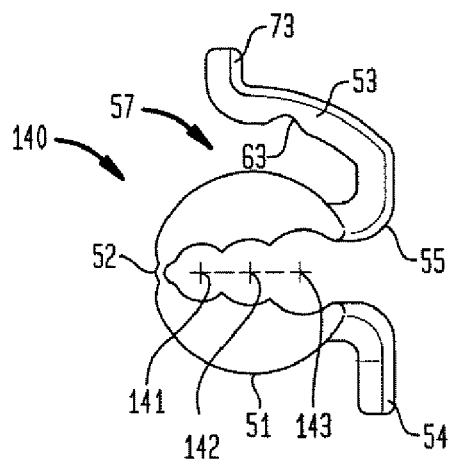

FIG. 19 shows a perspective view of an insert 140 according to the sixth embodiment for a clamping element 10 according to FIG. 1. FIG. 20 shows a side view of said insert 140 according to FIG. 19. The insert 140 has an upper clip 53 oriented in the direction of the connecting web 52, whereby between the clip 53 and the outer surface 56, there is a clamping space 57, into which a portion of the upper clamping jaw 13 intrudes. For these a groove 63 that runs lengthwise is provided in this latching space 57, which may be shaped complementary to a corresponding elevation in the clamping element 10. Furthermore, this thinning may enable an easier grip by the clip 53, as will be seen below.

The clip 53 may be shaped so that at rest, i.e. oriented in the direction of the outer surface, the insert 50, after its insertion in the clamping element 10 is held under initial tension by the clip 53. The length of the upper clip 53 is here almost as long as the width of the quarter cylinder 51. It has a base 73 at a slight distance from the clamping element 10 for easier gripping.

The lower clip 54, in contrast, is significantly shorter and is oriented perpendicular to the axis of the free space 11. The material thickness of the clips 53, 54 may be modified and other clip forms are possible. For this, reference may be made to the features of the descriptions of the other embodiments.

The connecting web 52 here shows a smaller radius of curvature than the jacket surfaces 56 of the elements 51. It is designed to be much thinner and when subjected to stress, buckles forward into the free space 11 or backwards out of the free space 11.

Particularly advantageous in this embodiment is the provision of several (two or more), here three, recesses 141, 142, and 143. These, identified as small, medium and large receiving grooves 141, 142, and 143, running in a transverse direction in the upper and lower portions of the inserts 140, permit the versatile insertion of the clamping element 10. In addition to the insertion of a rod of, for example, 15 millimeters in the clamping element 10 per se, by using a single insert 140, one can work with this clamping element with rods of, for example, 4, 5 or 6 millimeters diameters in the free spaces formed by grooves 141, 142 or 143.

The clamping is thus also advantageous in that in closing, the halves of the inserts generally become too displaced against each other, and less tilting of the insert halves 51 must take place. There is a smaller clamping distance than previously.

The arrangement of the three possibilities next to each other allows the surgeon to concentrate on the selection of the best pin-/rod material with respect to its size, and not to have to concern himself with questions of compatibility of the clamps. Naturally, it is also possible to provide only two alternative clamping grooves, which may also have diameters other than those mentioned. The smallest groove 141 is here the farthest away from the lateral insertion opening, so that the positions for laterally-inserted rods from the lateral opening through the groove 143 and on to groove 141 become smaller in each case. In principle, a reversed arrangement of the grooves is also possible, so that the grooves 141 for the smallest rod diameter are nearest to the entry areas 55.

Figure 21:
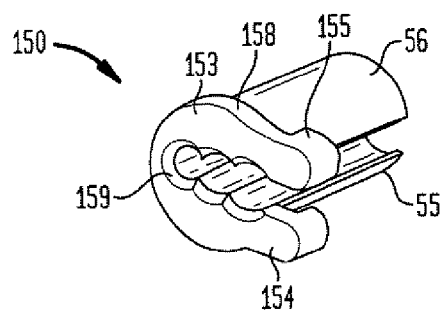
Figure 22:
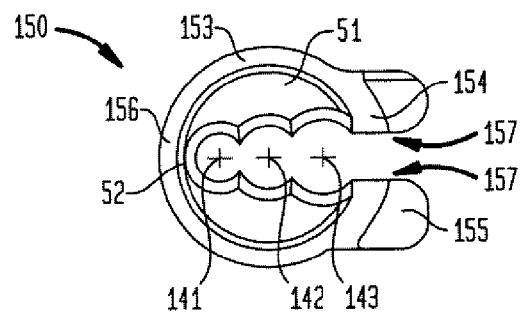
Figure 23:
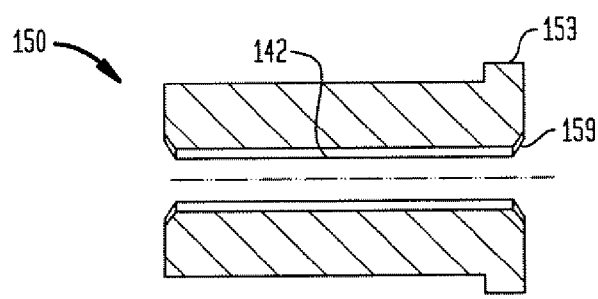

FIG. 21 shows a perspective view of an insert 150 according to a sixth embodiment for a clamping element 10 according to FIG. 1. FIG. 22 shows a side view of said insert 150 according to FIG. 21, and FIG. 23, a sectional front view of the insert 150.

The seventh embodiment has in common with the sixth embodiment described in FIGS. 19 and 20 the fact that there are three receiving grooves 141, 142 and 143, which extend along the main axis of the insert 150. The receiving grooves 141, 142 and 143 form in cross-section a sector with a radius of 4, 5 or 6 millimeters, the center of which lies on the median axis of insert 150. The smallest groove 141, which is the farthest from the lateral insertion opening, in fact fills in a three-quarters circle in cross section. This means that the web 52 is designed here as remaining material between the inner radius of the grooves 141 and the outer radius of the outer jacket surfaces 56.

Instead of a clip oriented toward the opening, a flange 153 is provided here on the one side, which is designed in a C-shape. It has free ends 154, which fit into complementary recesses in a clamping element. In particular, the free ends 154 each have a cam 155, which with its projecting step hooks in, and at the same time may form a gripping element. The connecting section 156 of the flange 153 that is opposite the free ends may in other embodiments also be made thinner or left out entirely, in order not to hinder the flexible movement of the web 52 in clamping. The front- and back-side openings in the grooves 141, 142 and 143 have bevels 159, in order to allow a longitudinal insertion of rods.

Thus this insert 150 has two opposing jacket elements 51 that define, across the lengthwise direction of the rod-shaped elements to be inserted, a sequence of here three longitudinal receiving grooves 141, 142, 143 for rod-shaped elements of varying diameters. For reasons of space, the distance of the midpoint of the circle of the receiving grooves 141, 142, 143 lying on the median axis of the insert is smaller than the diameter of the rod determined by it. The medium receiving groove 142 thus is concentric to the jacket surface 56 of the insert 150. The distance from this to the smaller receiving groove 142 next to the web is smaller than the distance to the larger receiving groove 143 next to the opening.

For an embodiment of a clamping element not shown in the drawings, the edge 158 that runs around the flange, particularly on the portions leading to the free ends 154, is essential. In this clamping element, which is not depicted, complementary outer surfaces of the clamping jaws 11 and 12 surround these edges 158 and full cams extend from the clamping jaws 11 and 12 and lie between the areas of the free ends 154, which are indicated by the reference number 157. Thus the clamping jaws 11 and 12 when clamped press the free ends 154 onto one another and onto the cams that are provided in the area 157. The clamping effect that is produced prevents the lengthwise displacement of the insert 150 and strengthens the holding quality, as the flange 153 itself is pressed by the clamping jaws 11, 12.

It should be stressed that the term embodiment in the aforementioned description does not mean that only the elements of the respective insert, clamping element or articulated elements are the subject of the invention. There are, in particular, also combinations of features that are possible, that are described in the subjects of various figures. Thus, the slots 85 can also be provided in the webs 52, 62; the clips 53, 54 may have the entire width of the inserts and may also be slotted, in order to go around the ribs 21; the clip 53 may also, like the side rib 92, be used in inserts 80, 90, and the side ribs 92 can form a side border to inserts 50, 60, 70. The scope of protection is thus not limited to the embodiments represented in the drawings, but may be taken only from the attached claims.

The invention claimed is:

1. An insert for a clamping element, the clamping element having two jaws to clamp a rod-shaped element, wherein the insert comprises:
    first and second jacket elements each adapted to be inserted between the two jaws with the first jacket element adjacent a first jaw and the second jacket element adjacent a second jaw of the two jaws of the clamping element to modify a space available for the rod-shaped element, and
    each of the first and second jacket elements having a retaining section, which fixes at least a portion of the insert on at least one of the first and second jaws of the clamping element, wherein the first and second jacket elements are connected to one another by a connecting web in the form of an undulating s-shaped web, the undulating s-shaped web having a first curved portion connected to each jacket element with an oppositely curved second portion connected to each first curved portion, the second curved portion extending into the space for receiving the rod-shaped element along a plane which is free from intersection with any other part of the insert.

2. The insert according to claim 1, wherein the first and second jacket elements are adapted to be inserted adjacent a respective one jaw of the first and second jaws thereby reducing the space available for said rod-shaped element.

3. The insert according to claim 1, wherein the connecting undulating s-shaped web forms a film hinge or meander-web.

4. The insert according to claim 1, wherein at least one retaining section comprises a portion surrounding an outer circumference of one of the first or second jaws and which portion extends generally parallel to a portion of the respective first or second jacket element defining the space for receiving the rod-shaped element.

5. The insert according to claim 4, wherein the retaining section on one of the first and second jacket elements has a retaining section which is formed as an element that can be gripped.

6. The insert according to claim 1, wherein the retaining sections are clips, and wherein the clips enclose portions of the first and second jaws between the jacket elements and the clips, said clips holding a jaw in a tight fit or under tension.

7. The insert according to claim 1, wherein the retaining sections are side ribs or front ribs or flanges, and wherein the side ribs or front ribs or flanges are enclosing portions of one of the first or second jaws between the jacket element and the rib or ribs or flanges, in a tight fit.

8. The insert according to claim 1, wherein the retaining section is formed on an end of each jacket element spaced from the connecting web.

9. The insert according to claim 1, wherein the inner side of one of the jacket elements has a shape on its inner side that is not concentric to its outer jacket surface.

10. The insert according to claim 9 wherein the inner side of one of the jacket elements has a concave shape.

11. The insert as claimed in claim 1, wherein the retaining section(s) are clips, and that portions of the jaws of the clamping elements between a jacket element and the clip are enclosed under tension.

12. The insert as claimed in claim 1, wherein one of the jacket elements has an inside surface with a concave shape on its inner side that is non-concentric to an outer jacket surface.

13. A clamping element comprising:
    first and second opposed jaws,
    one lateral open free space for laterally receiving a rod-shaped element,
    outer ribs that run transverse to said space,
    an insert, comprising:
    first and second jacket elements adapted to be inserted into each jaw of the clamping element to modify the space available for the rod-shaped element, wherein an inner surface of each jacket element comprises a concave rod-receiving portion adjacent a convex portion, the first and second jacket elements connected by an s-shaped undulating web, the s-shaped undulating web having a first curved portion connected adjacent to a respective convex portion of each jacket element with an oppositely curved second portion connected to each first curved portion, the second curved portion extending into the space for receiving the rod-shaped element and
    a retaining section, which fixes the insert or a portion of the insert in at least one of the jaws of the clamping element between said outer ribs.

14. The clamping element according to claim 13, comprising at least one slot that runs parallel to the said free space for receiving a clip of the insert.

15. An articulation element having first and second clamping elements, at least one of the two clamping elements comprising:
    first and second opposed jaws,
    one lateral open free space between the first and second jaws for laterally receiving a rod-shaped element,
    outer ribs that run transverse to said space,
    an insert, comprising:
    first and second jacket elements adapted to be inserted between the first and the second jaws to modify the space available for the rod-shaped element, the first jacket element in contact with the first jaw and the second jacket element in contact with the second jaw, the first and second jacket elements connected by an s-shaped undulating web, and
    each jacket element including a retaining section, which fixes the insert or a portion of the insert to at least one of the jaws of the clamping element between said outer ribs wherein the two clamping elements have first jaws oriented toward each other and are arranged one on top of the other.

16. An insert for a clamping element, the clamping element having two jaws to clamp a rod-shaped element, wherein the insert comprises:
    first and second jacket elements each adapted to be inserted between the two jaws with the first jacket element adjacent a first jaw and the second jacket element adjacent a second jaw of the two jaws of the clamping element to modify a space available for the rod-shaped element, and each of the first and second jacket elements having a retaining section, which fixes at least a portion of the insert on at least one of the first and second jaws of the clamping element wherein an inner surface of each jacket element comprises a concave rod receiving portion adjacent a convex portion, wherein the first and second jacket elements are connected to one another by a connecting web in the form of an undulating s-shaped web, the undulating s-shaped web having a first curved portion connected adjacent to a respective convex portion of each jacket element with an oppositely curved second portion connected to each first curved portion, the second curved portion extending into the space for receiving the rod-shaped element.

* * * * *